(12) United States Patent
Schmitz

(10) Patent No.: US 9,056,027 B2
(45) Date of Patent: Jun. 16, 2015

(54) ARTICLE COMPRISING A FLIPPED LEG HOOP AND PROCESS FOR THE MANUFACTURING OF SUCH ARTICLES

(76) Inventor: Christoph Schmitz, Euskirchen (DE)

( * ) Notice: Subject to any disclaimer, the term of this patent is extended or adjusted under 35 U.S.C. 154(b) by 886 days.

(21) Appl. No.: 12/451,509

(22) PCT Filed: May 14, 2008

(86) PCT No.: PCT/EP2008/003844
§ 371 (c)(1),
(2), (4) Date: Nov. 16, 2009

(87) PCT Pub. No.: WO2008/141756
PCT Pub. Date: Nov. 27, 2008

(65) Prior Publication Data
US 2010/0094236 A1   Apr. 15, 2010

(30) Foreign Application Priority Data
May 18, 2007 (WO) ............... PCT/EP2007/004447

(51) Int. Cl.
*A61F 13/15* (2006.01)
*A61F 13/20* (2006.01)

(52) U.S. Cl.
CPC ..... *A61F 13/15593* (2013.01); *Y10T 156/1051* (2015.01); *Y10T 156/10* (2015.01); *A61F 13/15585* (2013.01); *A61F 13/15747* (2013.01)

(58) Field of Classification Search
USPC ............. 604/385.01, 385.04, 385.101, 396
See application file for complete search history.

(56) References Cited

U.S. PATENT DOCUMENTS

| | | | | |
|---|---|---|---|---|
| 4,617,082 A * | 10/1986 | Oshefsky et al. | ............... | 156/447 |
| 4,675,016 A * | 6/1987 | Meuli et al. | ............... | 604/385.28 |
| 4,743,241 A * | 5/1988 | Igaue et al. | ............... | 604/385.26 |
| 4,786,346 A * | 11/1988 | Ales et al. | ............... | 156/160 |
| 4,915,767 A * | 4/1990 | Rajala et al. | ............... | 156/440 |
| 4,917,746 A * | 4/1990 | Kons et al. | ............... | 156/164 |
| 4,946,539 A * | 8/1990 | Ales et al. | ............... | 156/495 |
| 5,104,116 A * | 4/1992 | Pohjola | ............... | 271/185 |
| 5,147,487 A * | 9/1992 | Nomura et al. | ............... | 156/164 |
| 5,171,388 A * | 12/1992 | Hoffman et al. | ............... | 156/164 |
| 5,213,645 A * | 5/1993 | Nomura et al. | ............... | 156/164 |
| 5,224,405 A * | 7/1993 | Pohjola | ............... | 83/24 |
| 5,259,902 A * | 11/1993 | Muckenfuhs | ............... | 156/164 |
| 5,275,676 A * | 1/1994 | Rooyakkers et al. | ............... | 156/164 |
| 5,413,654 A * | 5/1995 | Igaue et al. | ............... | 156/161 |
| 5,500,075 A * | 3/1996 | Herrmann | ............... | 156/494 |
| 5,525,175 A * | 6/1996 | Blenke et al. | ............... | 156/161 |
| 6,098,557 A | 8/2000 | Couillard et al. | | |

(Continued)

FOREIGN PATENT DOCUMENTS

| | | |
|---|---|---|
| EP | 1224875 A1 | 7/2002 |
| EP | 1428487 A1 | 6/2004 |

(Continued)

*Primary Examiner* — Michele M Kidwell

(57) ABSTRACT

The present invention relates to articles such as pants or pant-like structures, which comprise leg hoops which are folded over along a fold line and which encircle the legs of a wearer during use, and to the manufacturing of such articles. Such manufacturing is particularly suitable for the making of diapers, training pants, adult incontinence articles, or other absorbent articles exhibiting a particular good body-conforming fit. The leg hoops are manufactured by flipping a part of the material, thereby creating the hoop structure as well as a body conforming shape of the article.

6 Claims, 16 Drawing Sheets

(56) References Cited

U.S. PATENT DOCUMENTS

2004/0102746 A1\* 5/2004 Mortell et al. ............... 604/358
2012/0042493 A1\* 2/2012 Schmitz ...................... 29/428

FOREIGN PATENT DOCUMENTS

| EP | 1552799 A1 | 7/2005 |
|---|---|---|
| WO | WO 2006/102974 A1 | 10/2006 |

\* cited by examiner

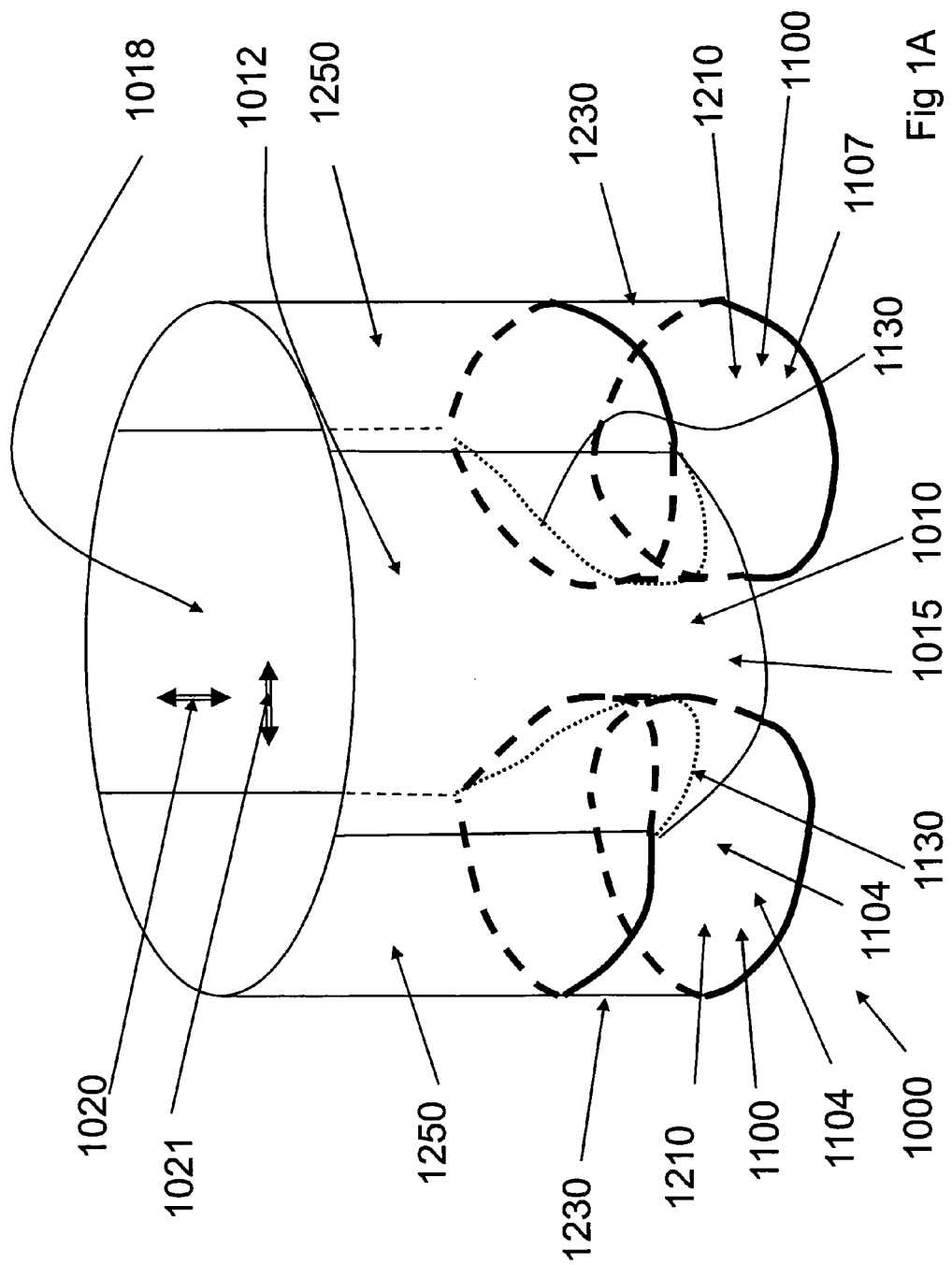

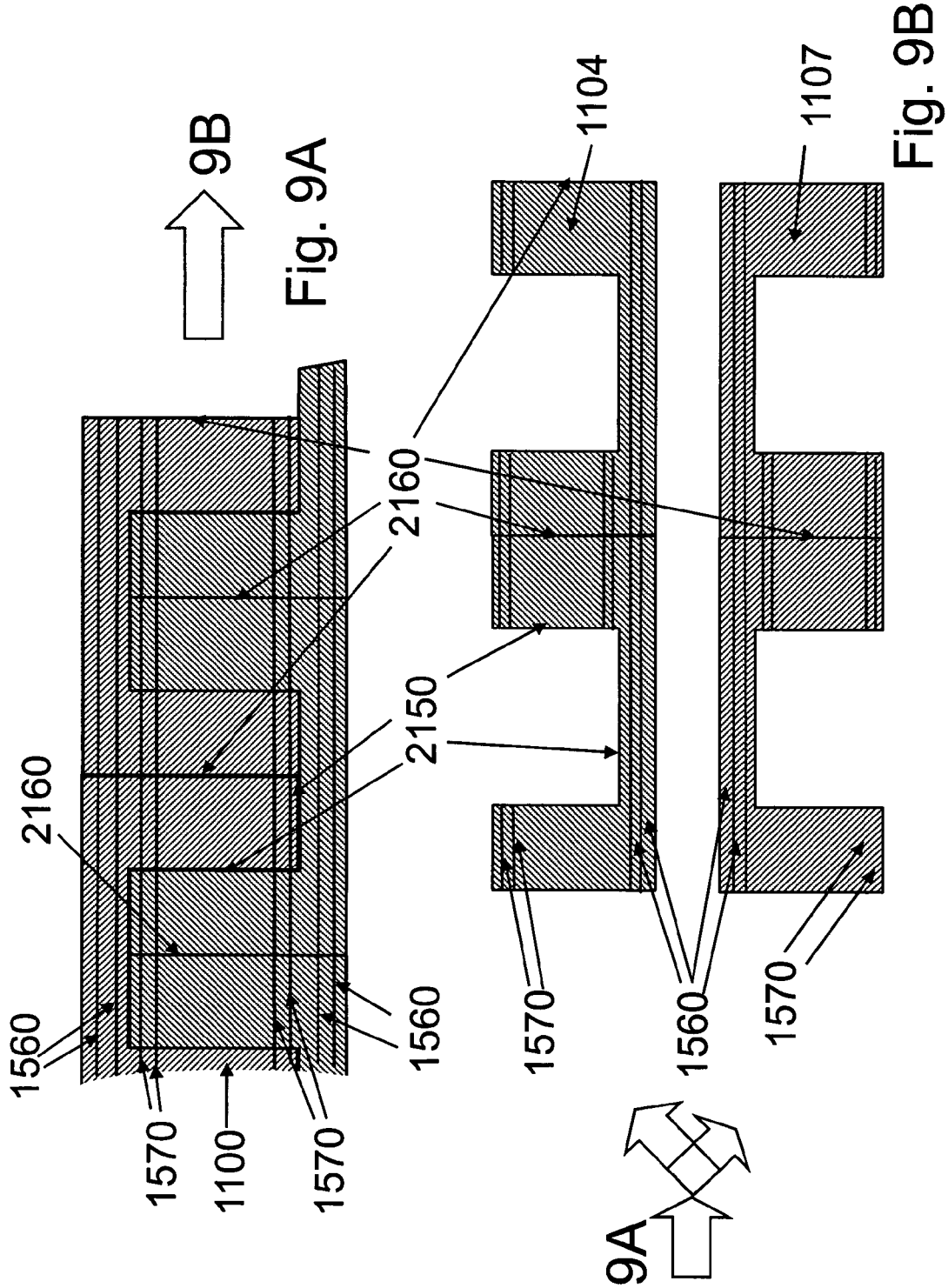

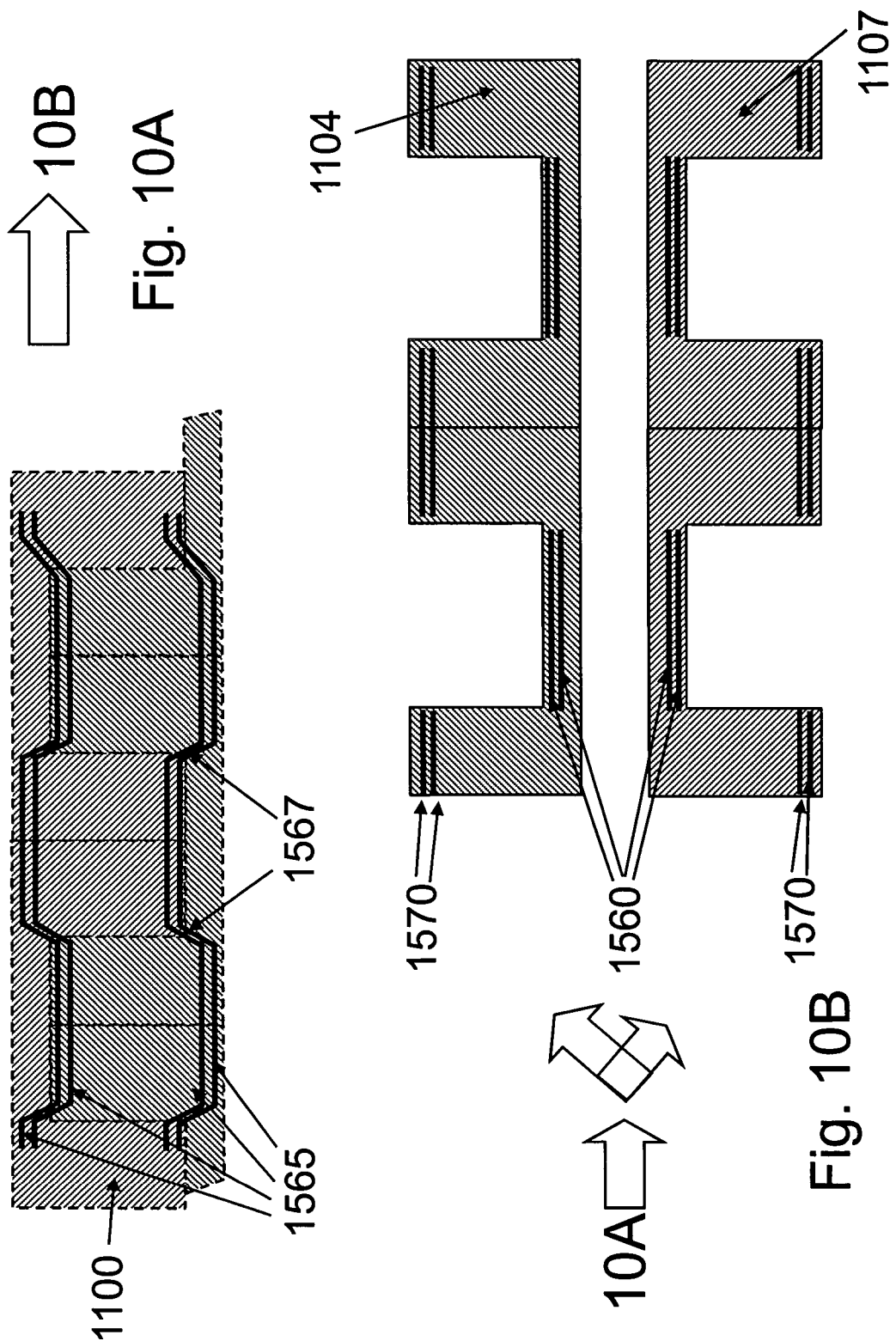

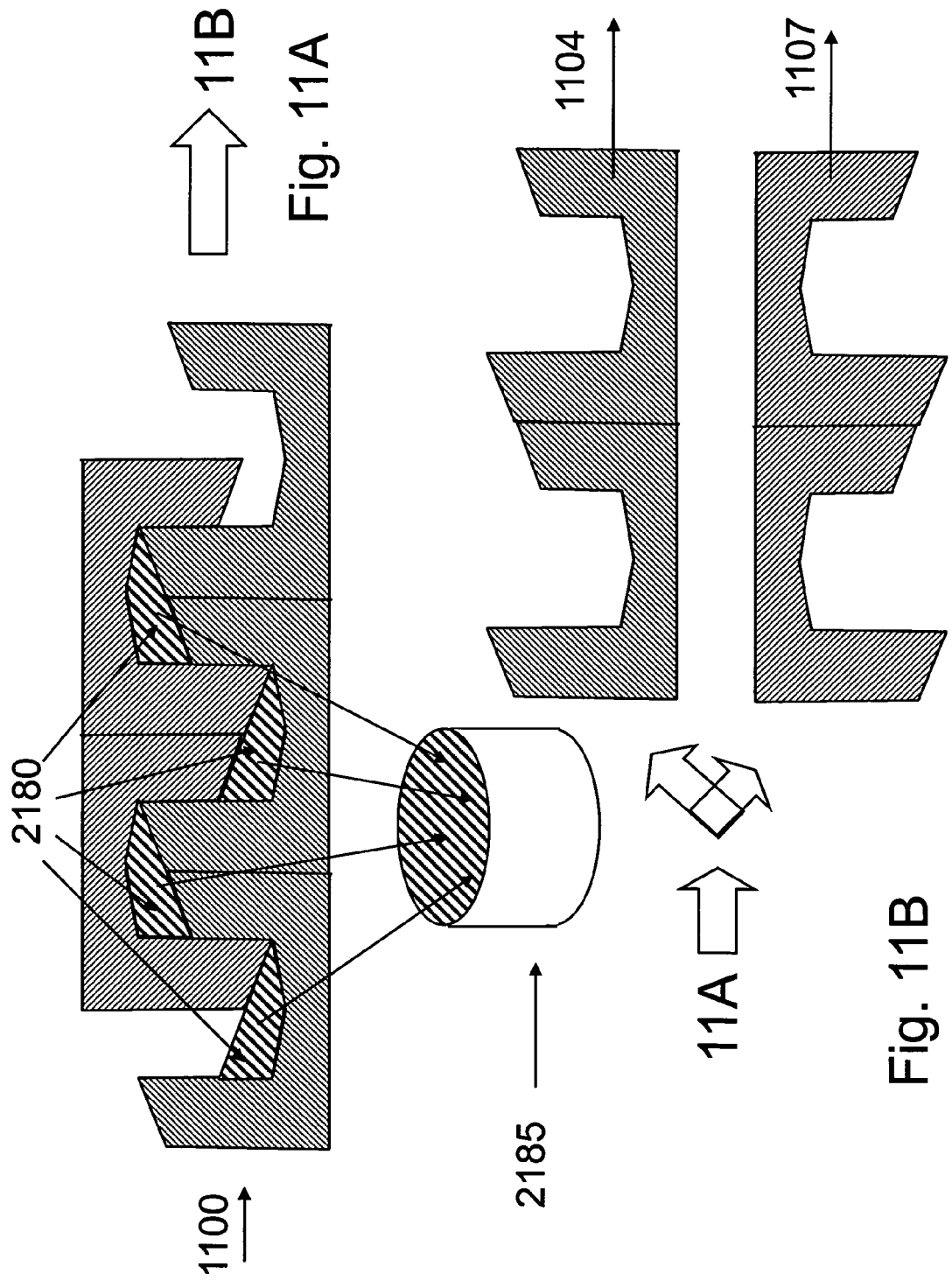

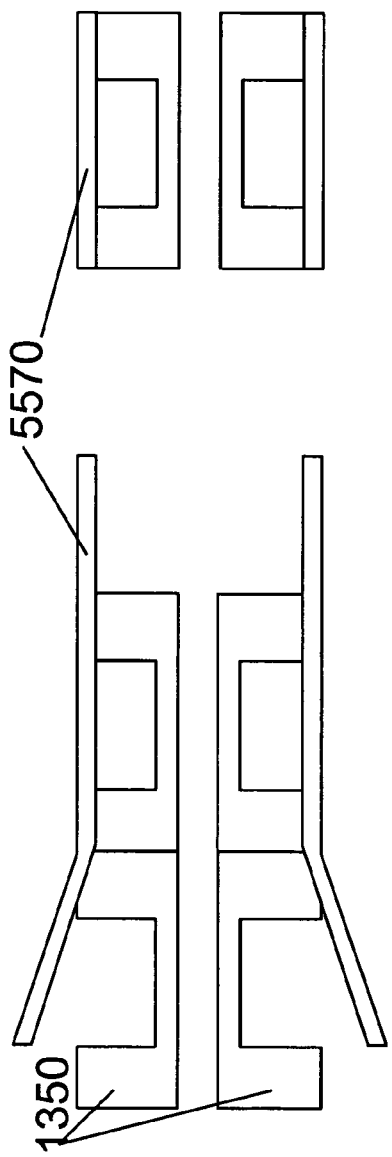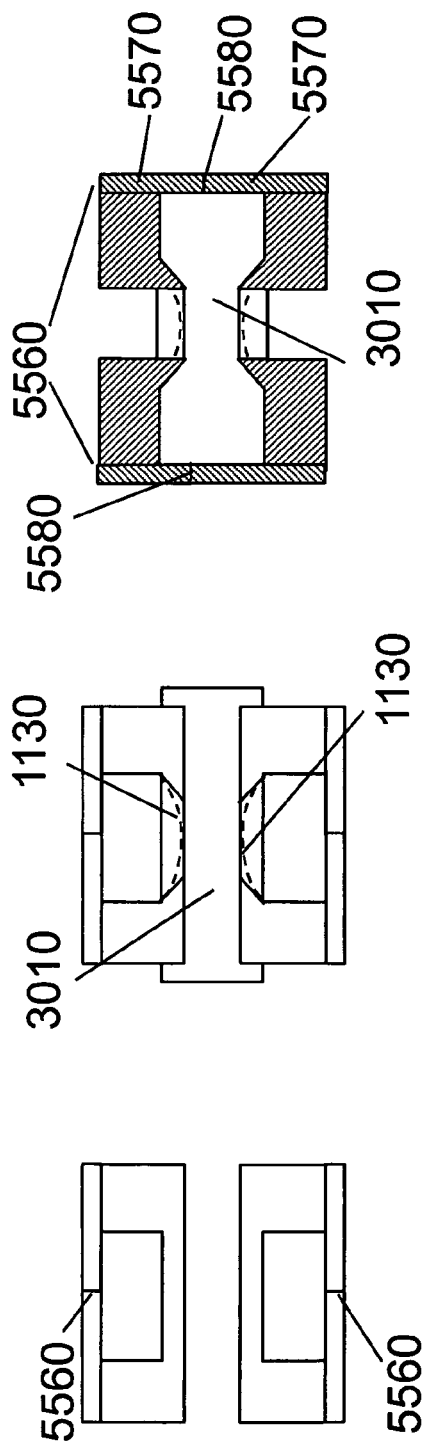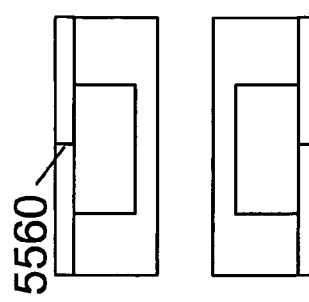

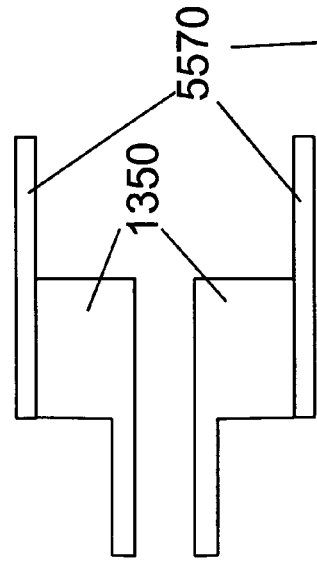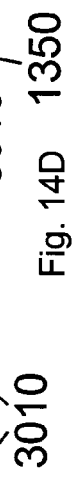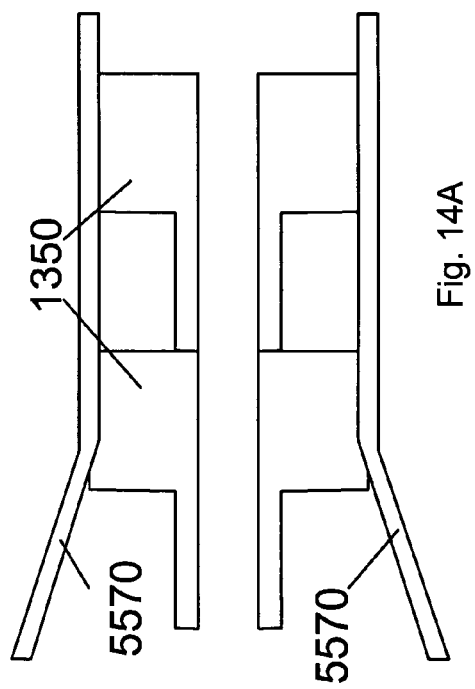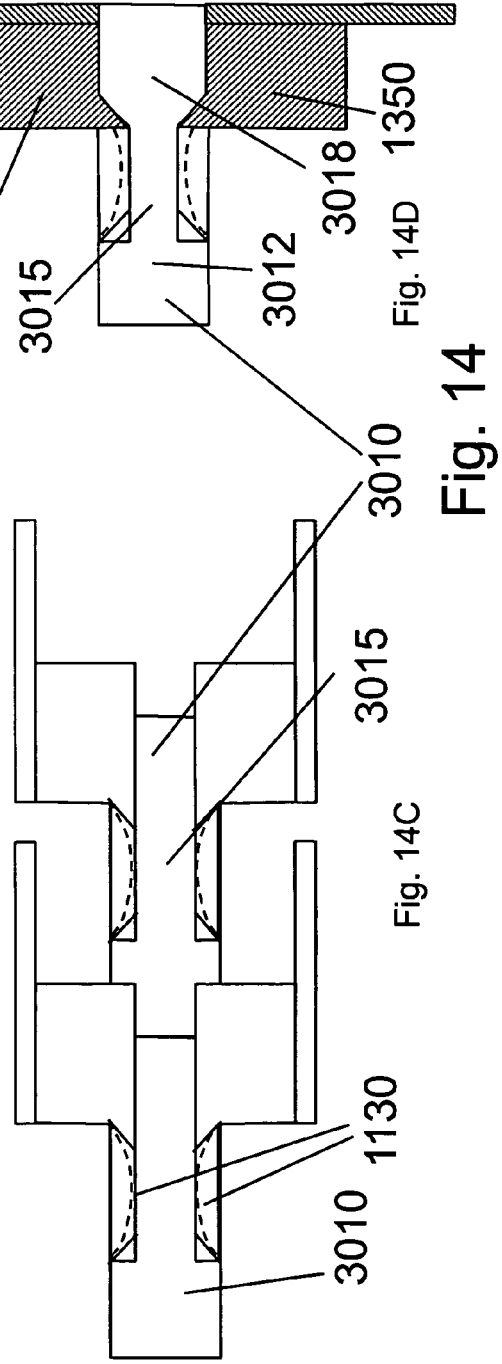
Fig. 14

ARTICLE COMPRISING A FLIPPED LEG HOOP AND PROCESS FOR THE MANUFACTURING OF SUCH ARTICLES

CROSS-REFERENCE TO RELATED APPLICATIONS

This application is a U.S. national phase application under 35 U.S.C. §37 based upon co-pending International Application No. PCT/EP2008/003844. Additionally, this U.S. national phase application claims the benefit of priority of co-pending International Application No. PCT/EP2007/003844 filed on May 14, 2008 and International Application No. PCT/EP2007/004447 filed on May 18, 2007. The entire disclosures of the prior applications are incorporated herein by reference. The international application was published on Nov. 27, 2008 under Publication Number WO 2008/141756 A1.

FIELD OF THE INVENTION

The present invention is the manufacture of articles such as pants or pant-like structures, which comprise elements encircling the legs of a wearer during use. Such manufacturing is particularly suitable for the making of diapers, training pants, adult incontinence articles or other absorbent articles exhibiting a particular good body-conforming fit.

BACKGROUND

Body conforming articles, such as 3D articles are known in the art—see e.g. WO 06/102974A1 or WO 08/037,281A1 in the name of C-4-S. Such articles can assume a body conforming shape by having leg features, such as leg cuffs or leg hoops, which are connected to the centre portion of the article along a curved connecting line. Upon donning of the article these leg features are up- or downwardly folded, such that they neatly conform to the shape of the legs of the wearer.

Manufacturing process and corresponding equipment arrangements for producing such articles are disclosed in the above mentioned publications WO 08/037,281A1 as well as in WO 06/103487A1 and WO 06/102973A1, all in the name of C-4-S.

One of the key differences of the processes as described in the above references to conventional processes is, that in the latter—such as described in EP1428487A1, EP1224875A1 or U.S. Pat. No. 6,098,557—an essentially continuous web is formed into an essentially continuous sequence of articles, which are separated not until just prior to the final step of packaging of the articles. The webs and articles remain essentially flat, whereby certain parts of the article may be flat folded onto other parts.

In contrast thereto, in the processes as described in the C-4-S publications, the articles are separated into individual articles earlier in the process sequence, and various elements or parts of the article are combined or bonded whilst a three-dimensional structure is formed, e.g. by means of forming heads.

Such equipment is very flexible in handling various product types and sizes. Whilst this set up is readily and efficiently achievable when constructing complete new manufacturing facilities, it is more difficult to be integrated into existing facilities.

Henceforth, it is an object of the present invention to provide a body conforming article, It is further object of the present invention, to provide a simple manufacturing process for body conforming articles comprising leg hoops which may even be realized by introducing minimal changes to existing conventional manufacturing lines, and articles produced by such a process.

SUMMARY

In one aspect, the present invention is an article for being worn on the lower torso of a wearer, which has
- a centre piece with a front, centre and rear region corresponding to a front, crotch, and rear region during use, and which defines the length direction and orientation of the article, and a width direction perpendicular thereto corresponding to the circumferential direction during use;
- a first and a second leg hoop for encircling the legs of a wearer during use;
- and optionally a first and a second side panel positioned in the lateral portions of the article, corresponding to the hip regions of the wearer during use.

Further, the leg hoops contain a material which is at least partly folded over preferably along a fold line of between 0° and 90°, preferably between 30° and 60° relative to the overall orientation of said material.

The leg hoops may be
- non-unitary with the centre piece and connected in the crotch region thereto, preferably by a curved connecting line, or
- unitary with the centre piece, or
- unitary with the side panel material.

Optionally, the article may further have a waist feature material for forming a waist hoop. In a second aspect, the present invention is a method for being carried out on a manufacturing equipment for the manufacture of an article for being worn on the lower torso of a wearer, wherein the article contains
- a centre piece with a front, centre and rear region corresponding to a front, crotch, and rear region during use, thereby defining the length direction and orientation of the article and a width direction perpendicular thereto corresponding to the circumferential direction during use;
- a first and a second leg hoop for encircling the legs of a wearer during use;
- optionally side panels positioned in the lateral portions of the article and corresponding to the hip regions of the wearer during use;
- optionally waist features for forming a waist hoop, The equipment has at least the following elements:
- a closed loop operating means defining a machine direction (closed loop operating means-MD);
- a flipping equipment attached to the closed loop operating means or otherwise operatively associated to the closed loop operating means to allow an essentially zero differential speed movement relative to the closed loop operating means and comprising a support plate rotatably mounted around a rotating axis, whereby the rotating axis is essentially co-planar with the closed loop operating means-MD and the width dimension of the article and at an angled orientation to the closed loop operating means-MD, preferably at an angle of between 0° and 90°, more preferably of between 30° and 60° relative to the closed loop operating means-MD, whereby the angle is measured as the smallest angle to the closed loop operating means-MD.

The method has at least the following steps, which not necessarily need to be executed in this order:
(a) providing
(i) a centre piece web material for forming the centre piece of the article exhibiting a centre piece machine directionality essentially aligned with the length direction of the article;
(ii) one or more leg hoop material(s) for forming the first and second leg hoop of the article by providing one or more separated leg hoop web material(s), essentially aligned with the MD direction of the centre piece web material, or by separating leg hoop regions out of the centre piece web material preferably by an essentially longitudinally oriented separating line, preferably a cut line terminating in the crotch region of the centre piece web material;
(iii) optionally providing side panel web material(s) which may be separate web materials or a region of the centre piece web material or a region of the leg hoop material;
(iv) optionally providing waist web materials;
(b) affixing at least a region of the leg hoop material(s) to a support plate of the flipping equipment,
(c) rotating the support plate around its rotating axis, such that a portion of the leg hoop material(s) is flipped over, thusly being oriented at an essentially different angle to the closed loop operating means-MD, preferably at an angle of between 60° and 120° relative to the orientation of the unflipped region(s) of the leg hoop material such that at least a portion of the leg hoop material is folded onto itself;
(d) optionally introducing side panel material;
(e) optionally connecting at least portions of the leg hoop materials to the centre and/or side panel material(s).

Optionally, the manufacturing method may further include other processing steps, such as:
- forming a pant like structure by forming a closed waist hoop;
- applying closure and/or fastening features;
- folding;
- packing;
- combing other web materials and/or web pieces and/or non web materials;
- combining liquid handling and/or absorbing materials.

An article according to the first aspect of the invention or made according to the second aspect, may be used as a body conforming pant, pant like article, absorbent article, baby or adult incontinence diaper, training pant, adult incontinence article, or feminine hygiene article.

BRIEF DESCRIPTION OF THE FIGURES

FIGS. 9 A & B schematically depict the process steps of separating a web of leg hoop material with elastic strands into separate webs for a fist and a second (integral) leg hoop/side panel.

FIGS. 10 A & B schematically depict the process steps as in FIG. 9 with a different elastic strand arrangement.

FIGS. 11A & B schematically depict the process steps to create an asymmetric integral leg hoop/side panel material.

FIGS. 13 and 14 depict schematically designs including a waist feature.

Corresponding numerals in various figures correspond to equivalent features.

DETAILED DESCRIPTION

In a first aspect, the present invention relates to articles such as pants or pant-like structures to be worn on the lower torso of a wearer, which comprise leg hoops, i.e. elements encircling the legs of a wearer during use, such as diapers, training pants, adult incontinence articles or other absorbent articles, which exhibit a particular good body-conforming fit.

Such body-conforming articles are described in the above mentioned publications WO 06/102974A1 or WO 08/037,281A1 to which explicit reference is made as to general teachings of use and constructions of such articles and basic process and equipment features, as well as general definition terms.

Such articles, which can be produced according to a second aspect of the present invention can be folded to an essentially flat structure, i.e. the body conforming shape is assumed just before unfolding the article prior to use or donning.

Figure 1B:
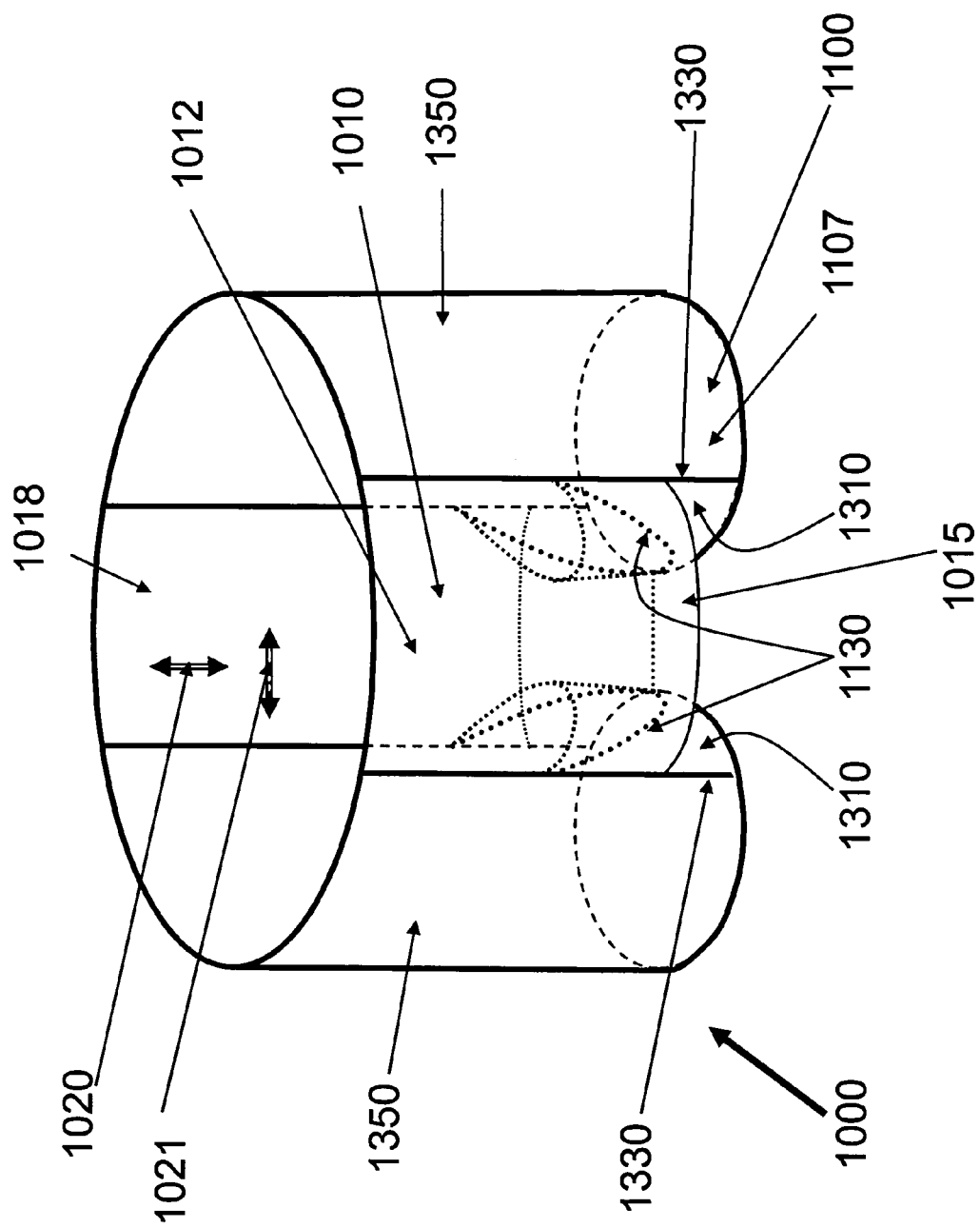
FIGS. 1A & B schematically show a perspective view of an article with a unitary and with a non-unitary leg hoop respectively.

FIGS. 1A and B show schematically a perspective view of an article, which suitably can be produced by the method according to the present invention. The article 1000 comprises a centre piece 1010 comprising a front waist region 1012, a crotch region 1015 and a back waist region 1018 corresponding to the regions of the wearer during use. The article exhibits generally a length direction 1020—defined by the sequence of front, crotch, and rear regions, and a width direction 1021 of said article perpendicular thereto, essentially aligned with a left—right orientation on the wearer.

The centre piece 1010 may be a unitary structure, although often it will be composed of various materials, such as backsheets, topsheets, absorbent cores embedded between topsheet and backsheet, so called secondary topsheets, barrier leg cuffs, absorbent elements, closure elements and the like, all well known to a skilled person.

During use, the article may be in a closed loop (or hoop) arrangement around the waist of the wearer. As shown in FIGS. 1A and B, side panels 1250 and 1350 respectively may be connected to the centre piece and/or themselves, either permanently or releasably. Thus, the article may be a fully closed pant, a pre-closed pant, which may be opened by the user, or may be an open pad which may be closed e.g. by adhesive tapes or so called mechanical fasteners around the waist of the wearer, as typically done with conventional baby diapers or adult incontinence articles.

In the context of the present invention, the articles comprise leg hoops, i.e. closed structures 1100 encircling the legs of a wearer during use. A first 1104 and a second leg hoop 1107 correspond to a right and a left leg hoop during use.

Within the present context, the term "unitary leg hoop" refers to a design (see FIG. 1A) wherein an essentially unitary piece of material 1210 fully encircles the leg, which is further connected at least to the crotch region 1015 of the centre piece 1010 of the article. As shown in FIG. 1A, it may be connected to itself, e.g. by a hoop connecting line 1230. As exemplarily shown in FIG. 1A, the side panel material 1250 can extend from the front and rear ends of the article towards the leg hoop material 1210 and may be connected thereto. Optionally, the leg hoop material may be elasticized at least in a direction corresponding to the circumference of the leg.

The term "non-unitary leg hoop" refers to a similar design (see to FIG. 1B), except that the full encircling of the leg is achieved by a combination of a hoop material 1310, which is connected to the centre piece 1010, and at least a further material to complete the encircling of the leg, here shown as an extension of the side panel material 1350 by hoop connecting line 1330. Here, the leg hoop material 1310 is connected to the crotch region 1015 of the centre piece, and may be elasticized at least in a direction corresponding to the circumference of the leg. This allows a reduced usage of elasticized material compared to the unitary leg hoop design.

Within the current context, the term "hoop material" refers to the materials 1210 and 1310, which may be connected to the crotch region of the centre piece. As described in the hereinabove referenced C-4-S publications, the connecting is achieved by a curve-linear connecting line 1130. Alternatively, the connecting may be achieved by a connecting region with curve-linear boundaries. This will—even when performed in the flat state during manufacturing—create a body conforming structure, upon donning of the article. The connecting can be performed by various connecting means, such as thermo-, pressure-, or ultrasonic-bonding, or by application of adhesives or glues, as well known in the art.

In yet a further embodiment, the leg hoops may be formed from parts of the centre piece, as will be described in more detail herein below (see also FIG. 15). In this case, the intersections of centre crotch area and leg areas form curve-linear fold-lines when the product is on the wearer.

Figure 2A:
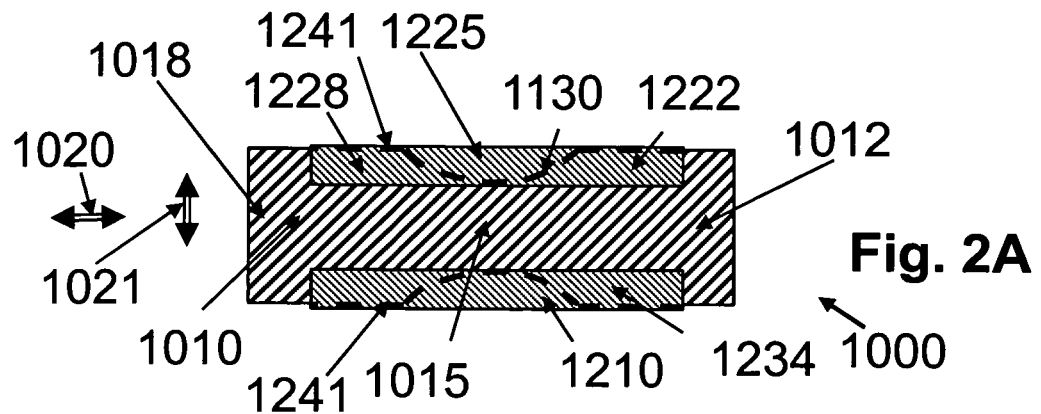
FIGS. 2 A-C schematically show a top view of an article with a unitary leg hoop, cut open and laid flat.
Figure 2B:
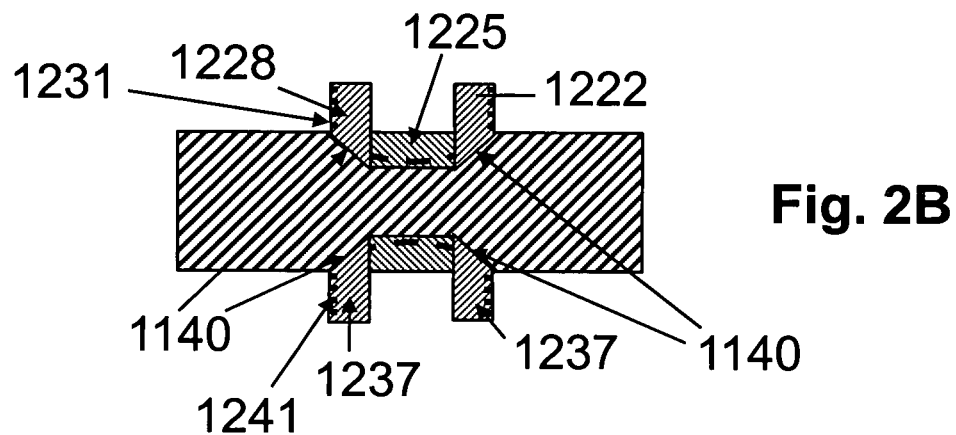
Figure 2C:
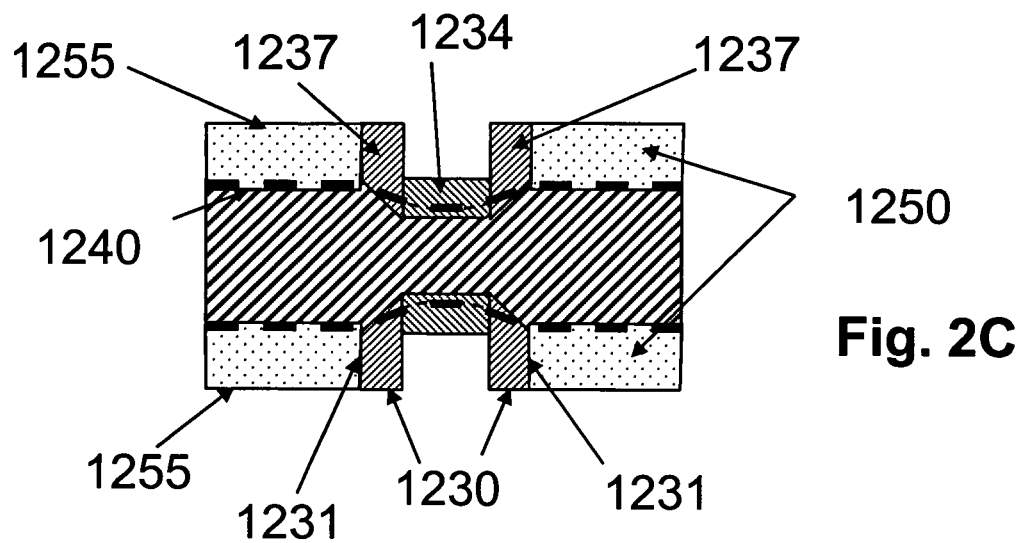
Figure 3A:
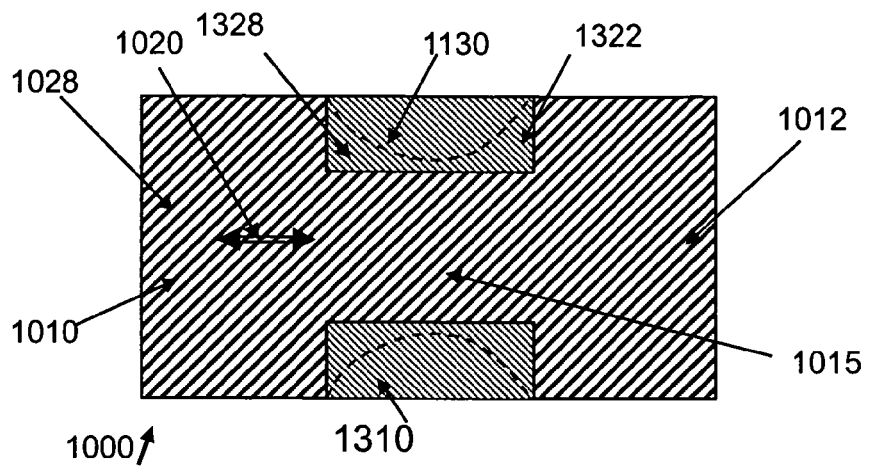
FIGS. 3 A-C schematically show a top view of an article with a non-unitary leg hoop, cut open and laid flat.
Figure 3B:
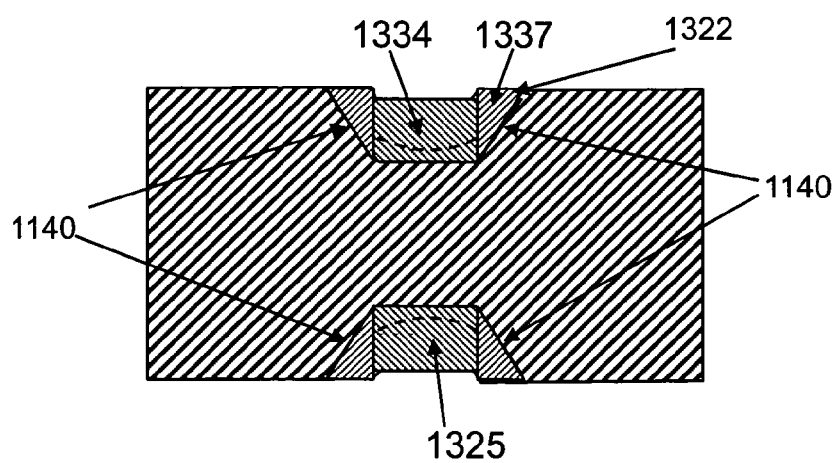

When considering a cut open and flat projection of the articles as shown in FIG. 1, structures as depicted schematically in FIG. 2 (unitary leg hoop design) and FIG. 3 (non-unitary leg hoop design) result. Even though these and the following figures show pieces of webs which correspond to the pieces of an article, it should be kept in mind, that during the key process steps as presently described, consecutive centre pieces still form an essentially endless web material.

FIGS. 2 and 3 show the centre piece 1010 overlaid by the leg hoop material 1210 and 1310 respectively, as these are transferred from their supply means to the centre piece. They may already be connected to the crotch region 1015 of the centre piece by a curve-linear connecting line 1130. The materials extend in longitudinal direction forwardly and rearwardly beyond the region where they are connected to the centre piece, refer to forward (1222 resp. 1322) and rearward (1228 resp. 1328) leg hoop extensions.

During the process of the present invention, these extensions are at least partially flipped, i.e. they are folded over along a fold line 1140 which is angled by more than 0° but less than 90° relative to the overall orientation of the material, which is typically though not necessarily aligned with the longitudinal direction of the article, preferably between about 30° and 60°, more preferably at about 45°. Within the present context, this angle of the folding line is considered to be always the smallest angle between any orientation of the folding line with any orientation of the longitudinal axis. For the example as shown in the FIGS. 2B and 3B, the angle of the fold line both for the left and right and front and rear extensions is shown as 45° and the flipping of the extensions will change the orientation of the material by 90°, i.e. the material as positioned along a length orientation of the article prior to flipping will extend along the width orientation thereafter. Accordingly, when the fold line is at an angle of between 30° and 60°, the orientation of the material after being flipped will be between 60° and 120° relative to its position prior to flipping. As the fold line will typically intersect the longitudinal edge of the centre piece at about the delimitation of the crotch regions from the front respectively rear regions of the centre piece, at least a certain part of the leg hoop material initially overlaying the crotch region of the centre piece will be folded over and thus belong to the flipped extension. In a non-unitary leg hoop design (FIG. 3), the extensions may terminate after flipping essentially close to the longitudinal side margin of the crotch region 1015 of the centre piece, whilst in a unitary leg hoop design (FIG. 2), they will project laterally outwardly. Upon such folding over, a top view will now show the original upper surface (1234 and 1334 respectively) in the crotch region (1225 resp. 1325) and the original opposite surfaces (1237 and 1337 respectively) in the flipped extension regions (1222, 1228 and 1322, 1328 respectively).

Figure 15A:
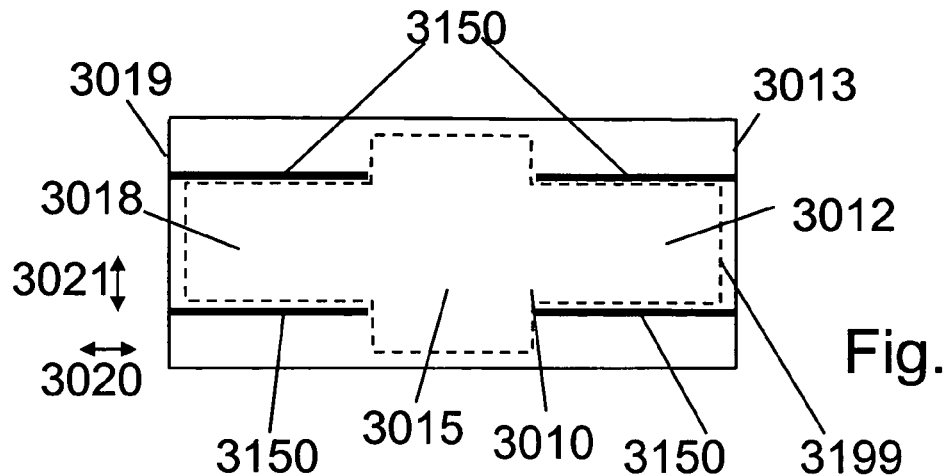
FIGS. 15 A, B, and C schematically depict a further embodiment for an article according to the present invention.
Figure 15B:
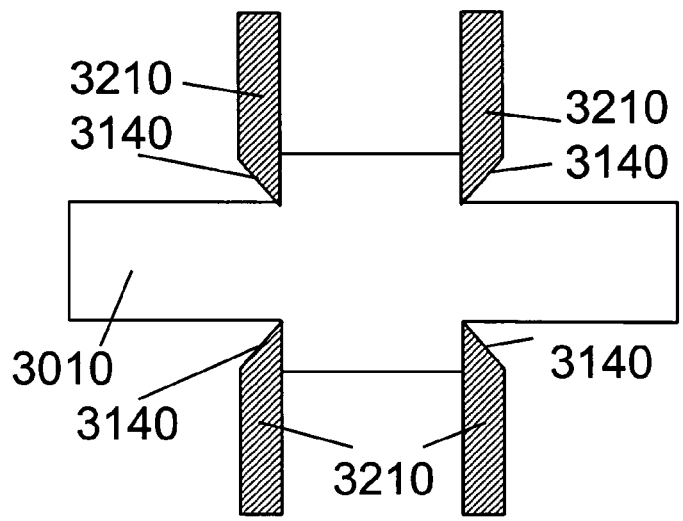
Figure 15C:
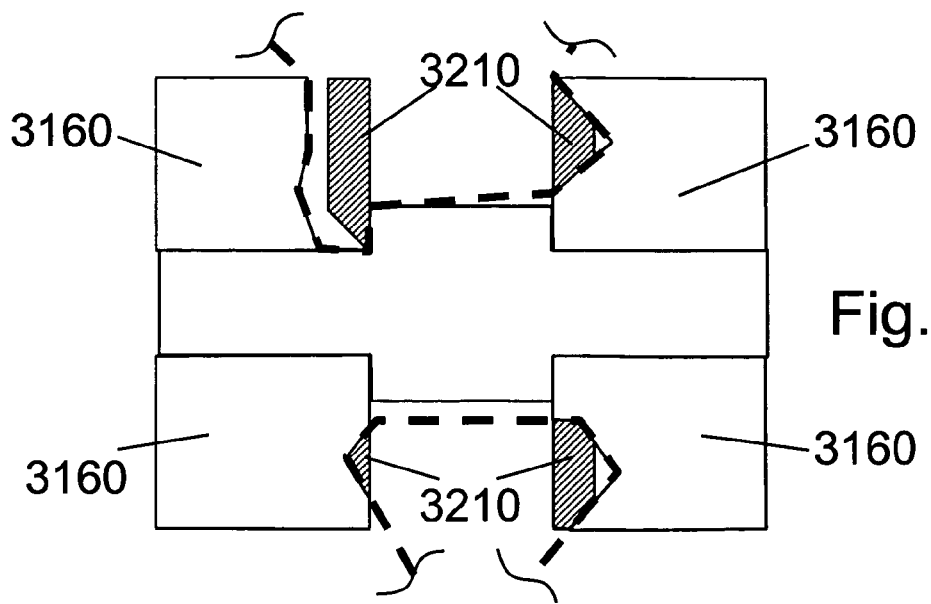

In a further design as depicted in FIG. 15, no additional material is required to form the leg hoops, but a part of the centre piece material is partly cut apart and flipped, whilst still being partly connected to the centre piece. To this end, a centre piece material 3010 with a front (3012), crotch (3015) and rear (3018) region exhibiting a machine direction 3020 and a cross-machine direction 3021, is provided. Four cuts 3150 are made, such as by conventional cutting means, starting from the left and right portions of the front and rear margins, 3013 and 3019 respectively, and running towards the crotch region where they terminate without completely separating the stripe.

The cuts may run parallel to the longitudinal axis 3020, or may be made in an angled arrangement. If the cuts do not end in the laterally extending front or rear margins in the front and back waist areas 3013 and 3019, cross directional cuts can be made in the partly cut away areas to separate the leading end of the next article from the trailing end of the previous article in these particular areas. The cuts may all be symmetrical, but may also have longer or shorter length and/or cross-directional positioning, respectively. The partly cut loose stripes are then flipped at the end of the cut line around a fold line 3140 by flipping equipment as described herein below, such that they extend outwardly thereby forming the leg hoops 3210, whilst the area 3199 as marked in FIG. 15 A remains unflipped. The overall length of the centre piece as well as the length and the positioning of the cut lines 3150 are adjusted so as to provide appropriate fit lengthwise as well as circumferentially around the waist and the legs.

Figure 3C:
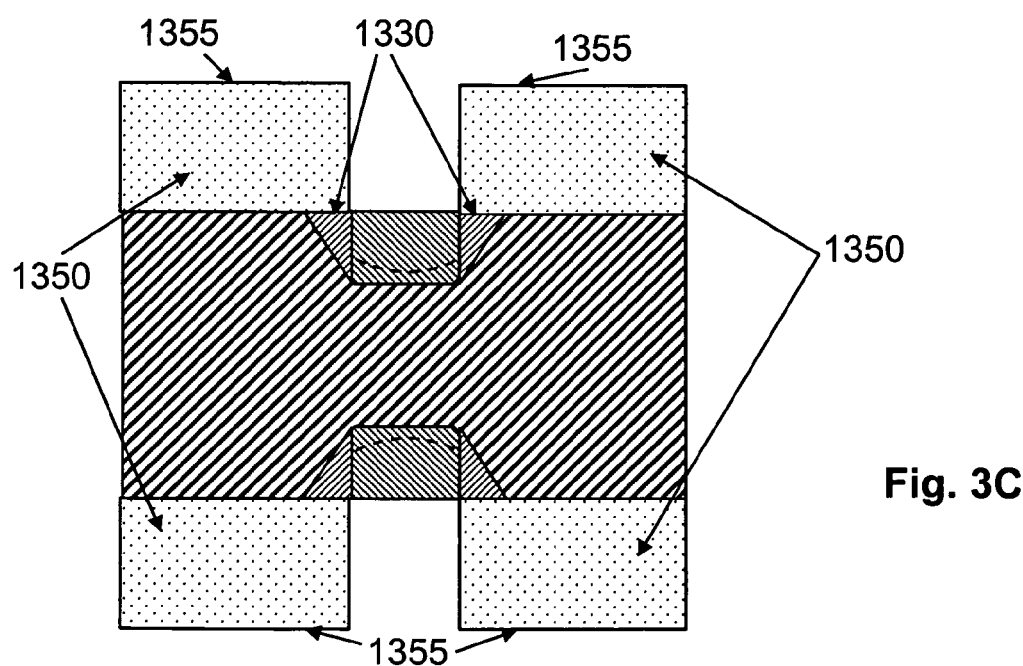
Figure 4A:
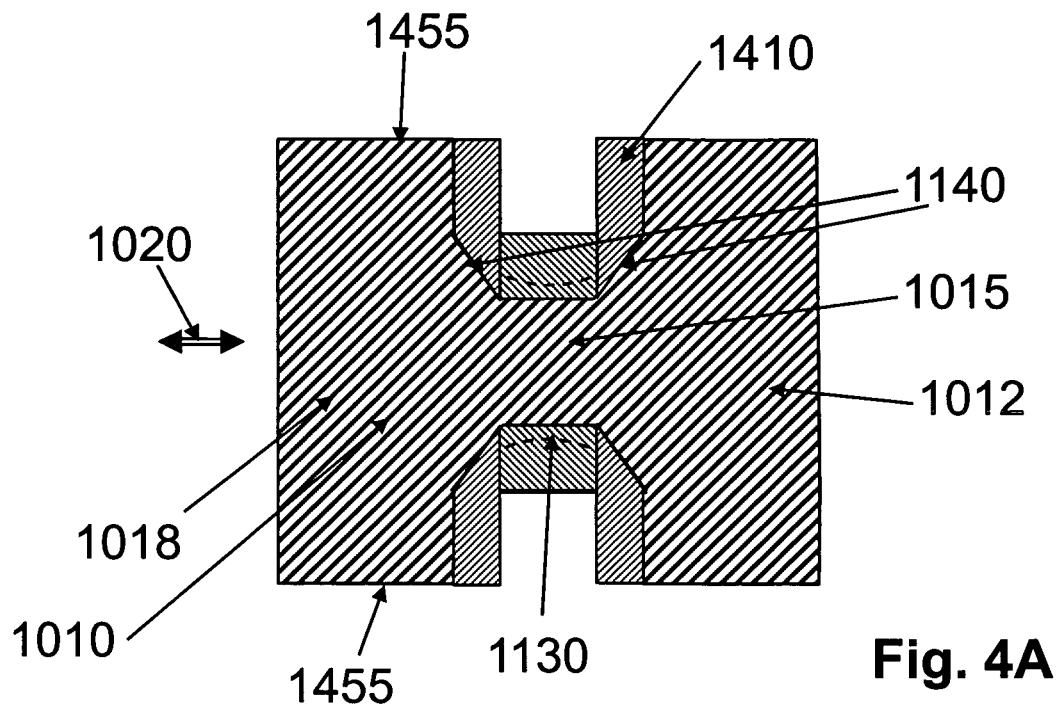
FIGS. 4 A & B schematically show a top view of an hourglass shaped article, cut open and laid flat.
Figure 4B:
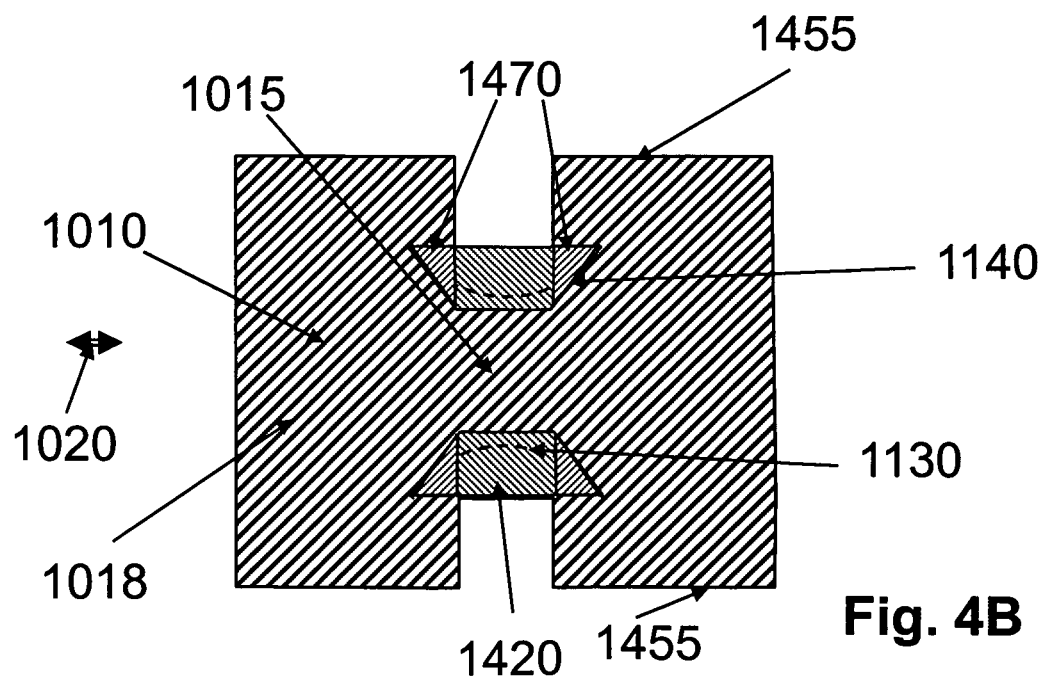

In addition to the centre piece and the leg hoop materials, the article comprises side panels in various alternatives:

In a first embodiment as shown in FIGS. 2C and 3C, the hip or side panels (1250 and 1350 respectively) are separate pieces of material, and connected to the centre piece 1010 of the article during the process of the present invention by suitable connecting means, such as adhesive bonding. For a unitary hoop design, the panels are connected to the leg hoop material 1210, forming the leg hoop by being connected, e.g. by hoop connecting line 1230, and may also be connected to themselves respectively along their corresponding adjacent longitudinal edges 1255 and 1355 respectively. They may also be connected to the unitary hoop material along lines 1231. For a non-unitary hoop design, the panels are connected to the leg hoop material 1310 along their inner longitudinal edges along hoop connecting line 1330. In another embodiment (refer to FIG. 4), the side panels are essentially unitary with the centre piece 1010 and extend laterally outwardly from in the front (1012) and rear (1018) regions, as if leg cut-outs are removed from an essentially rectangular piece of material, which then forms the centre piece 1010 integrally comprising the side panels. Such articles are typically referred to as "hourglass shaped". Included in this embodiment is a variant, wherein the side panels are pre-assembled to the centre piece, i.e. formed before the material is provided to the process according to one aspect of the present invention. Also this embodiment may be executed in both leg hoop design variant—see FIG. 4A for the unitary leg hoop design with a unitary leg hoop 1410 and see FIG. 4B for the non-unitary leg hoop design with a non-unitary hoop material 1420. The leg hoop may be flipped along fold line 1140. For a unitary leg hoop design, it may be connected to the centre piece and to itself. For a non-unitary leg hoop design, it may be connected to the centre piece along a cut-line 1470.

Figure 5A:
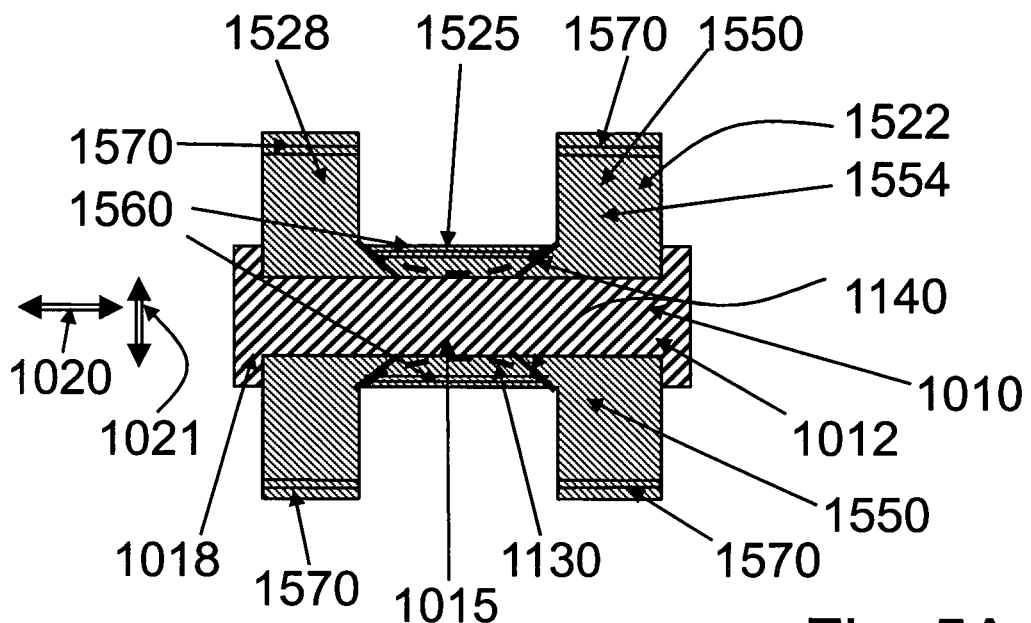
FIGS. 5 A & B schematically show a top view of an article with an integral hoop and side panel, cut open and laid flat.
Figure 5B:
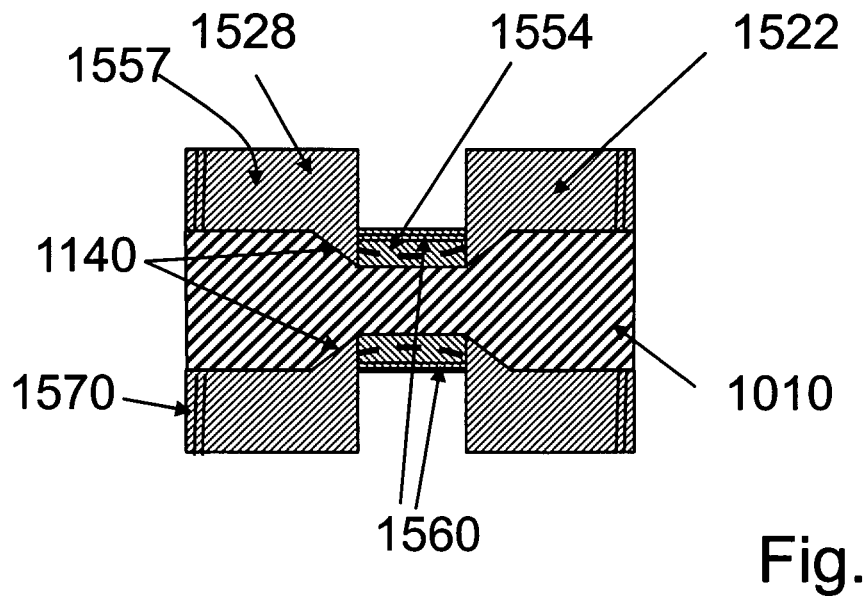

In a further embodiment, the hip or side panels are essentially integral with the (unitary) leg hoop material (see FIG. 5). As shown in an exemplary design in FIG. 5A, the integral leg hoop/side panel material 1550 is shown in a U-shape prior to the flipping, here already connected to the centre piece 1010 along a curve-linear connecting line 1130. Upon flipping of the forward (1522) and rearward (1528) extensions along fold line 1140—here shown in a 45° angle design—the extensions now form both the side panels as well as the leg hoop in the article, with their reverse surface 1557 being seen in the FIG. 5B. In the crotch region 1525, the original MD orientation of the material still corresponds to the longitudinal orientation 1020 of the article and the originally upwardly facing surface 1554 can be seen. However, in the flipped extension regions, i.e. in the side-panel and leg hoop regions, the original MD orientation of the material corresponds to the width orientation of the article 1021. This is of particular advantage, if the side panel material comprises an elastically extensible material, e.g. an elastic thread. This can be applied to the extensions and elongated by a simple MD stretching process prior to the flipping, such that these materials can deliver width contraction in the article after flipping. This is exemplified in FIG. 5 by elastic threads for the leg hoop region (1560) and for the waist region (1570) respectively.

In the design as shown in FIG. 15, FIG. 15 C shows in a partly cut away section the flipped leg hoops 3210, being overlaid by the side panels 3160. These are connected to the front respectively rear portion of the centre piece as well as to the flipped parts now forming the hoop 3210.

Whilst not necessarily preferred, any combination of these embodiments can be applied and is considered to also fall within the scope of the present invention, e.g. integral side panels for the rear region (forming a T-shape), and separate panels are attached in the front region, or less pronounced integral side extensions may be combined with separate panels.

As the skilled person in the field of manufacturing pants, pant like garments, or absorbent articles will readily appreciate, the article may comprise further elements as commonly known or readily applicable or used in such garments, such as elastic elements, closure elements, absorbent elements, optionally removable or replaceable, various coversheet elements, such as topsheets, secondary topsheets and the like, various backsheet alternatives, such as plastic films, or nonwovens, or laminate combinations thereof, etc.

Figure 6:
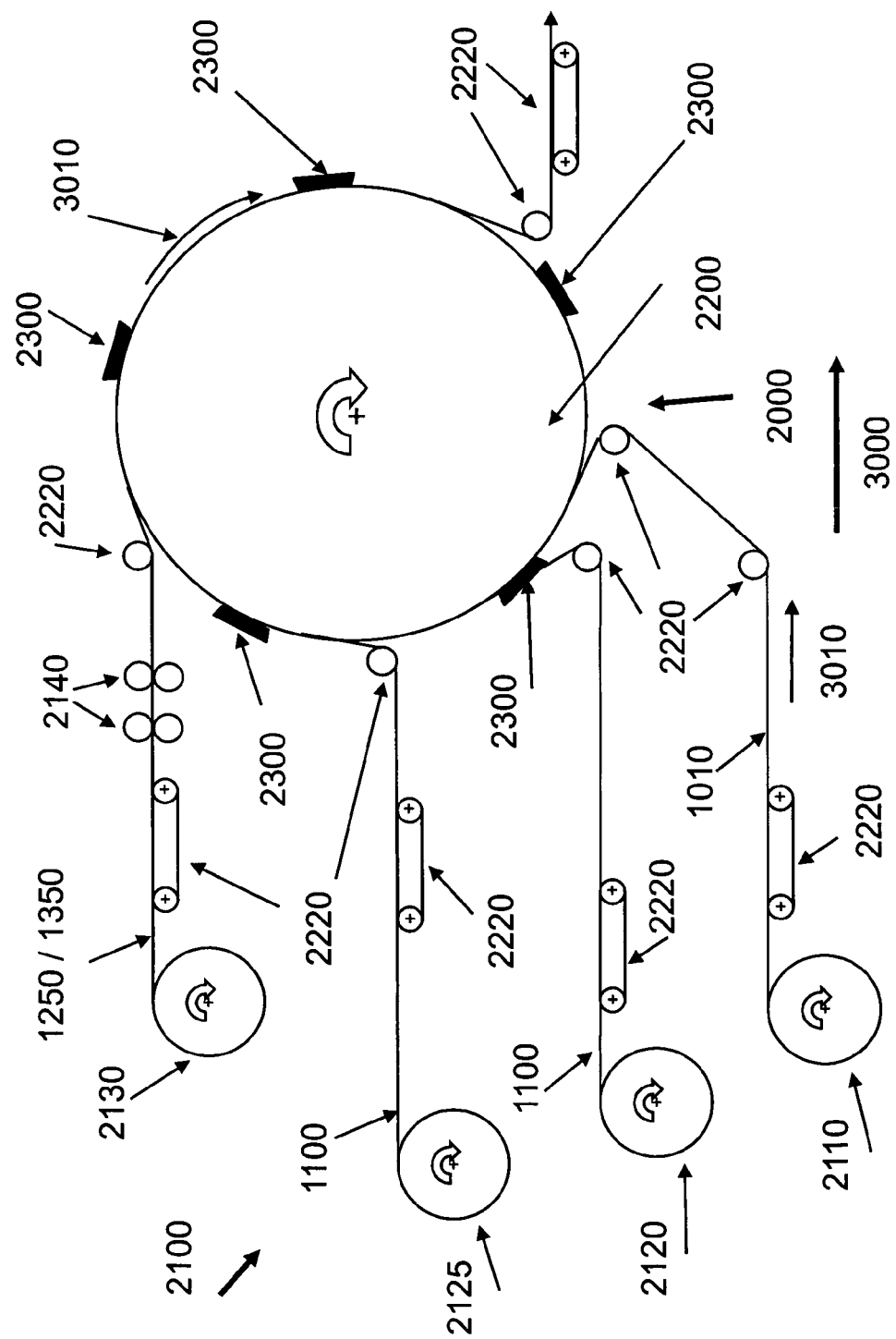
FIG. 6 schematically shows the equipment set up for a process according to the present invention.

For the purpose of executing the present invention, the following elements for a manufacturing equipment 2000 are required (ref. to FIG. 6).

The materials need to be supplied to the operating unit by material supply means. Preferably, all materials will be delivered as continuous respectively web materials or threads, i.e. essentially endless materials, preferably delivered in roll from, although other delivery forms are suitable too, such as spools or a meandering arrangement in boxes. Henceforth, the supply means comprise conventional equipment elements, such as unwinding or unspooling stands (2110, 2120, 2125, 2130), or so-called de-festooning box feeders. Additionally, the equipment may comprise guiding and support means (2220) for the materials.

A further element of the equipment set up is a closed loop operating means 2200, comprising an endless surface onto which the web materials may be applied. The closed loop operating means comprises an essentially continuous moveable surface, whereby the direction of movement is aligned with the machine direction 3010 of the centre piece material, and hence also with the longitudinal direction of the article 1020. The closed loop means may be an essentially endless belt, running over at least two guide rolls or drums. In may also be a series of web support means, which may also be arranged as described the C-4-S patent application published as WO 06/103487, e.g. to allow production of varying length articles on one equipment. In a preferred embodiment, the closed loop means has a drum shape and rotates around its longitudinal axis, also referred to as a turret. The width of the belt or of the drum may be at least the width of the article.

The apparatus further comprises flipping equipment 2300 for folding the leg hoop material.

Whilst various equipments for performing such operation are known, a first preferred arrangement is described in the above references WO 06/102973 A1, see in particular FIG. 19 and the corresponding description.

An even more preferred equipment is a mechanical flipping device 2300, see also FIG. 7, showing exemplarily the flipping in the context of a design with an integral leg hoop and side panel, as depicted in FIG. 5, and in FIG. 8 for a unitary leg hoop design as depicted in FIGS. 1A and 2.

Figure 7A:
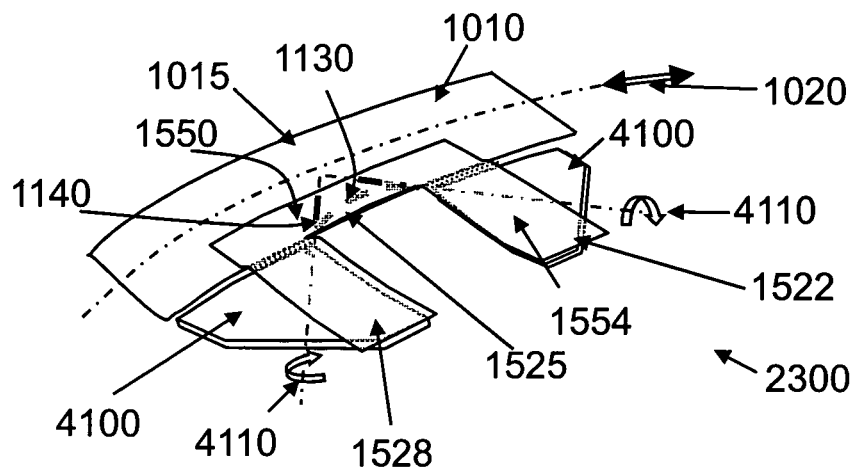
FIGS. 7 A-C schematically show equipment for flipping integral leg hoops and side panels, and respective process steps.
Figure 7B:
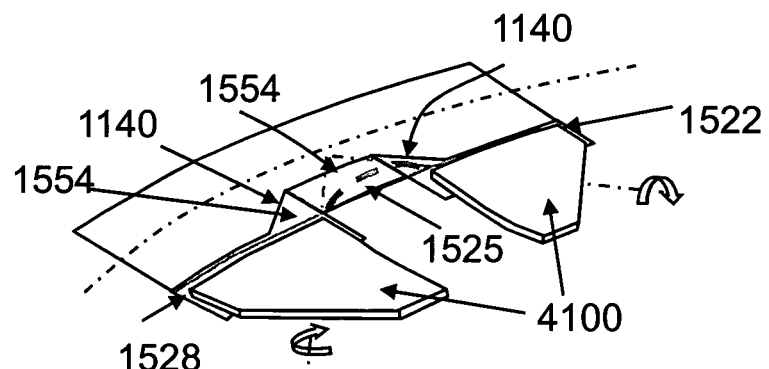

This equipment design comprises a support plate 4100 for each extension, which is to be flipped. The plate is moveably connected to the operating means (not shown) so as to essentially extend laterally outwardly levelled with the outer surface of the operating means. As depicted in FIG. 7A, plates 4100 are designed such that the extensions 1522 and 1528 respectively of the integral leg hoop/side panel material 1550 can be laid essentially flat there onto, whilst the crotch region 1525 overlays the crotch region 1015 of the centre piece material 1010, optionally already affixed and connected thereto by a curve-linear connecting line 1130. The support plates may comprise hold-down means so as to affix the material to the surface, such as controllable vacuum suction means (not shown). Each support plate is rotatably arranged around axis 4110. Approximating the surface segment of the operating means by a plane (i.e. neglecting for example the curvature of the turret in this section), the axis 4110 is positioned essentially co-planar with the surface of the operating means or x-,y-plane (i.e. defined by longitudinal and width direction) of the centre piece. The axis is further parallel to the fold line 1140, here shown at a 45° angle to the longitudinal direction 1020.

As shown in FIG. 7A, the integral leg hoop/side panel material 1550 is positioned onto the support plate, with its first surface 1554 facing upwardly.

After rotating the support plate by 180° (see FIG. 7B), the flipped extensions have changed their orientation, and the opposite surface 1557 is now facing upwards, and the rotated support plate overlays this material.

The shape of the support plate does not need to correspond exactly to the shape of the extension, it is, however, important that the parts next to connection lines or regions are well supported and guided during the flipping. Preferably, the support plate is retractable along a cross-directional orientation 4120 of the apparatus so as to ease removal of the article further downstream (see FIG. 7C).

FIG. 8 A to C show a corresponding set up for a non-unitary design, with hoop material 1210 with longitudinal extension 1222 and 1228. The hoop material is connected to the crotch region 1015 of the centre piece by a connecting line 1130. The support plates 4100 are positioned such that they can be rotatably moved onto the leg hoop material overlaying the centrepiece. Upon affixing the leg hoop material extensions to the support plates—e.g. by vacuum suction—the support plates can be rotated back, thus flipping the extensions. As shown in FIG. 8D, the separate side panels may be added. Optionally, the support plates may be arranged such that they are laterally moveable.

Further, the process according to the present invention requires connecting means for affixing various elements to each other.

In particular, the leg hoop materials need to be connected to the centre piece. If separate side panels are included in the design, these need to be connected to the centre piece and to the leg hoop materials.

This connecting can be achieved by various equipments well known to a person skilled in the art, such as thermo-bonding or ultrasonic bonding, if the material combinations allow such bonding.

A preferred embodiment comprises glue or adhesive bonding where conventional adhesives such as hot melt adhesives may be applied by glue spray nozzles, glue bead applicators, so called curtain coater, glue printer, or other conventional equipment. In a particular preferred embodiment, a glued bead applicator is moveable along the CD-orientation of the article when this is moving underneath the glue applicator.

Additional equipment may be further employed, as will be readily apparent for the person skilled in the art.

In general terms, the process as will be further explained by referring to FIGS. 6 to 11, comprises steps of:
 providing the required materials;
 transferring them to a closed loop operating means and positioning them in a particular arrangement;
 flipping the leg hoop material;
 connecting corresponding materials.

Whilst in the following description the individual required process steps are arranged in a certain logical order, this does not necessarily correspond to the chronological order or the process flow direction.

The materials may be provided in conventional manners.

The centre piece material for the article can be provided in any conventional procedures for supplying essentially endless web materials, such as unwinding from rolls (2110), or spools, or out of boxes. These materials exhibit a first material machine directionality 3010, which is aligned to correspond to the longitudinal direction of the article.

A material for the leg hoops may also be provided in similar conventional manners for supplying a web material. The material may be provided in various embodiments.

In a first embodiment, a first and a second web material for the first and the second leg hoop of the article are separately supplied, e.g. each from a roll unwinding stand (2120/2125 respectively). After being separated to the appropriate length, the hoop material will typically, but not necessarily form essentially rectangular or trapezoidal pieces.

In a second embodiment, the materials may be supplied in a combined form from e.g. one roll, and the web may be separated so as to form the material for the first and second leg hoop. This separation may be along a straight longitudinal line e.g. the longitudinal centreline of the material.

The separation may also be along a non-straight line so as to form—preferably intermeshing—pieces for the first and second leg hoop, respectively. For example, as shown in FIG. 9A, a continuous web material 1100 may be separated along a meandering line 2150, and upon phasing and guiding, an essentially endless series of shaped material pieces results, which may further be separated along lines 2160 to provide essentially mirror symmetrical pieces, here for an integral leg hoop/side panel material 1110. As shown in FIG. 10, the material does not need to be separated to longitudinally symmetrical elements, but when accepting a certain amount of scrap or trim 2180, the asymmetric U-shape allows an article design, which fits on the wearer e.g. lower in the front waist region as compared to the rear waist region.

The leg hoop material may be an essentially unitary web, such as a non-woven web material. It may also be a composite material, such as a non-woven combined with a polymeric film or with threads 1560. The material or the composite may also be elastically extensible, e.g. along its machine direction. This stretching can be achieved by conventional means, such as indicated by two consecutive nips 2140 running at a speed differential.

The elastic may also be applied to the leg hoop material also in a meandering way, as exemplified in FIG. 10 showing elastic threads 1565 which may result in both a waist and a leg hoop elastification, as further explained in FIG. 5. Alternatively, elastic threads may be applied in a direction parallel to the machine direction. The non-woven carrier may be flat, or folded over on one or both sides, e.g. to cover the elastic threads.

As the leg hoop materials as well as the side panel materials will be attached to the continuous centre piece material after they are separated to individual pieces, it is considered to be within the scope of the present invention, if these pieces are not separated from web materials as described herein above, but also delivered already in a pre-separated state.

The materials are transferred towards the closed loop operating unit by conventional transfer and guide means 2220, such as web support means as endless belts, optionally with web holding means such as vacuum means, and/or guide rolls or bars.

The closed loop operating means—in the preferred embodiment a turret—may be operated at a surface speed of more than 5 m/sec and may be as high 10 msec. The direction of movement 3010 is essentially aligned with the MD direction of the centre piece material or the longitudinal direction of the article 1020. In the overall process direction 3000, the centre piece material is first fed to the outer surface of the closed loop operating unit 2200 at a "matching speed", such that the material has essentially no relative movement to the surface. This may further be supported by holdings means as well known in the art such as vacuum suction. Further, the leg hoop materials are fed to the closed loop operating unit 2200 essentially such that their machine direction is parallel to the machine direction of said centre piece web material.

A further element of the process is the combining of the respective materials, i.e. the positioning of the materials relative to each other.

To this end, the leg hoop materials need to be separated to the predetermined appropriate length and phased to the right position to the geometry of the centre piece by conventional means.

The first and second leg hoop materials may be positioned in an essentially mirror-symmetrical and cross-directional spaced apart arrangement onto the centre piece material, such that a first portion of the leg hoop materials is positioned in the crotch region of the article, and front and rear extensions extend forwardly and rearwardly respectively, and such that the first and said second leg hoop materials are positioned along the longitudinal edges of said centre region (see FIGS. 2 to 5).

The side panel materials are fed to the closed loop operating unit depending on the particular design embodiment of the finished article as described hereinabove.

The leg hoop material will under go a flipping step.

In an exemplary explanation for this process step, a unitary leg hoop/side panel material 1550 is considered (see FIG. 7).

As shown in FIG. 7A, the forward and rearward extensions 1522 and 1528 respectively of the integral leg hoop/side panel material 1550 are each positioned and optionally affixed such as by vacuum onto a support plate 4100, with their first surface 1554 facing upwardly, whilst the crotch region 1525 is overlaying the crotch region 1015 of the centre piece.

After rotating the support plate 4100 by 180° (see FIG. 7B), the flipped extensions have changed their orientation, and the opposite surface 1557 is now facing upwards, and the rotated support plate overlays this material. Subsequently, the forward and rearward extensions are fixed to the centre piece.

Figure 7C:
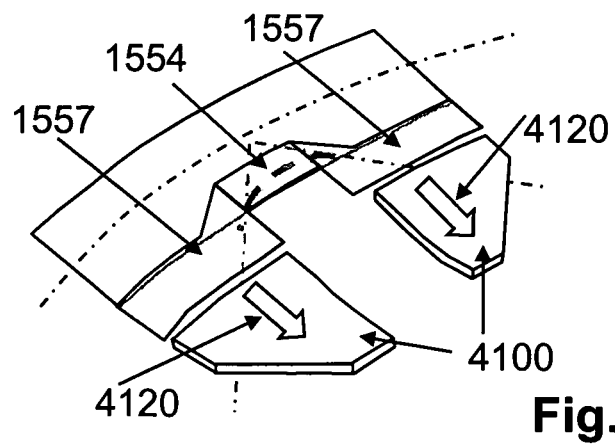
Figure 8A:
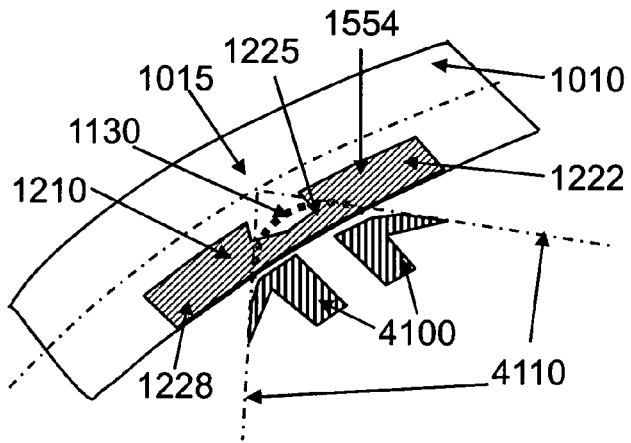
FIGS. 8 A-D schematically show equipment for flipping unitary leg hoops, and respective process steps.
Figure 8B:
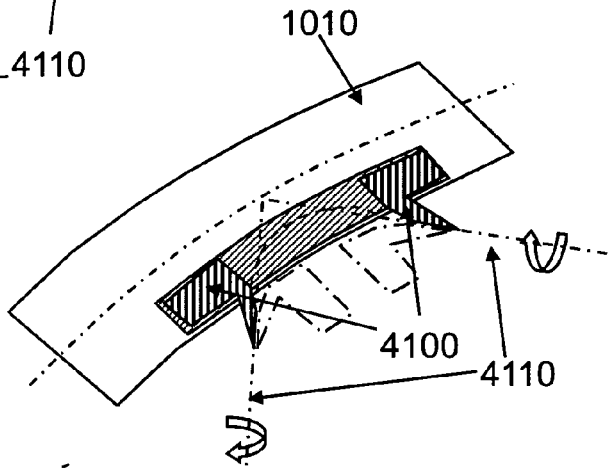
Figure 8C:
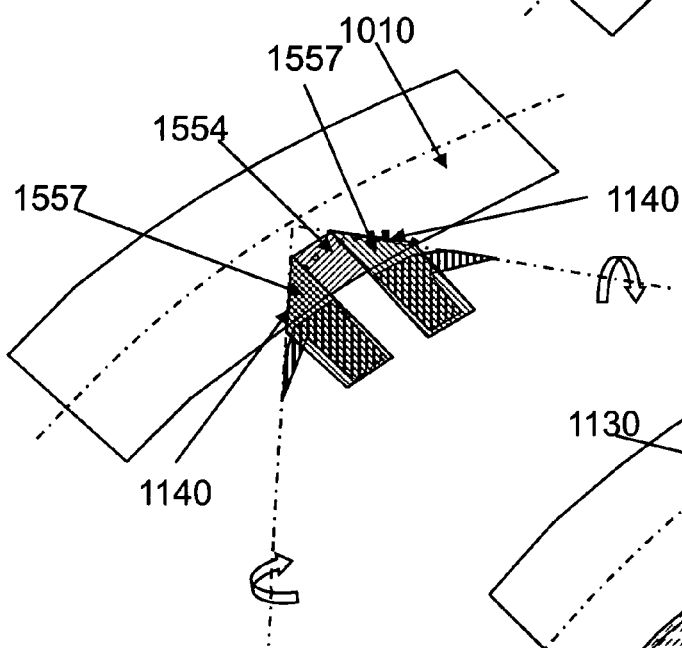
Figure 8D:
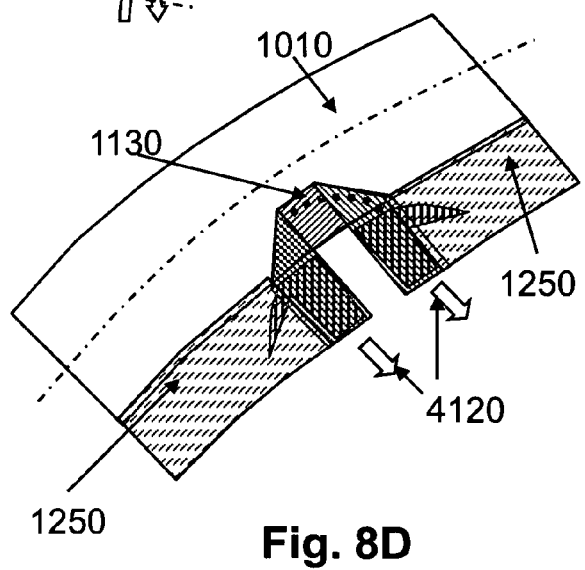

The support plate may then be retracted, e.g. along a cross-directional orientation 4120 of the apparatus so as to ease removal of the article further downstream (see FIG. 7C).

FIG. 8 illustrate the flipping process for a non-unitary leg hoop design variant. The process is essentially the same as described for FIG. 7, except that support plate 4100 contacts the leg hoop material by rotation towards the material after that is positioned on and optionally already connected to the centre piece 1010.

FIGS. 9 to 11 illustrate a particularly advantageous process element of splitting one web 1100 into a first and second integral leg hoop/side panel materials 1104 and 1107.

In FIG. 9 A, the web 1100 is pre-combined with each two pairs of—optionally pre-stretched—elastic strands for the leg hoop 1560 and for both the leg and the waist hoop 1570. This combined web material is separated by a meandering separation line, in FIG. 9A indicated by line 2150. After this separation is done, the web is split and at least one of the resulting webs is appropriately re-phased and re-directed, such that the webs 1104 and 1107 are positioned relatively to each other as indicated in FIG. 9B, which after cutting along lines 2160 may form a U-shaped integral leg hoop/side panel material 1550 as shown in FIG. 5. Alternatively, as shown in FIG. 10 A, the elastics 1560 and 1570 may be replaced by a combined leg and waist elastic material 1565, which may be guided along a meandering line, and which will be separated at separation point 1567 to provide the design as shown in FIG. 10B. Yet a further embodiment is indicated in FIG. 11, where the meandering separation line 2160 of FIG. 9 A is executed such that pieces 2180 are cut out, which may be collected in a collection box 2185 for adequate recycling. As shown in FIG. 11 B, such a design may result in asymmetrically shaped leg hoop/side panel materials 1104 and 1107, which will create a finished article, which fits e.g. lower in the front waist portion than in the back waist portion.

Figure 12A:
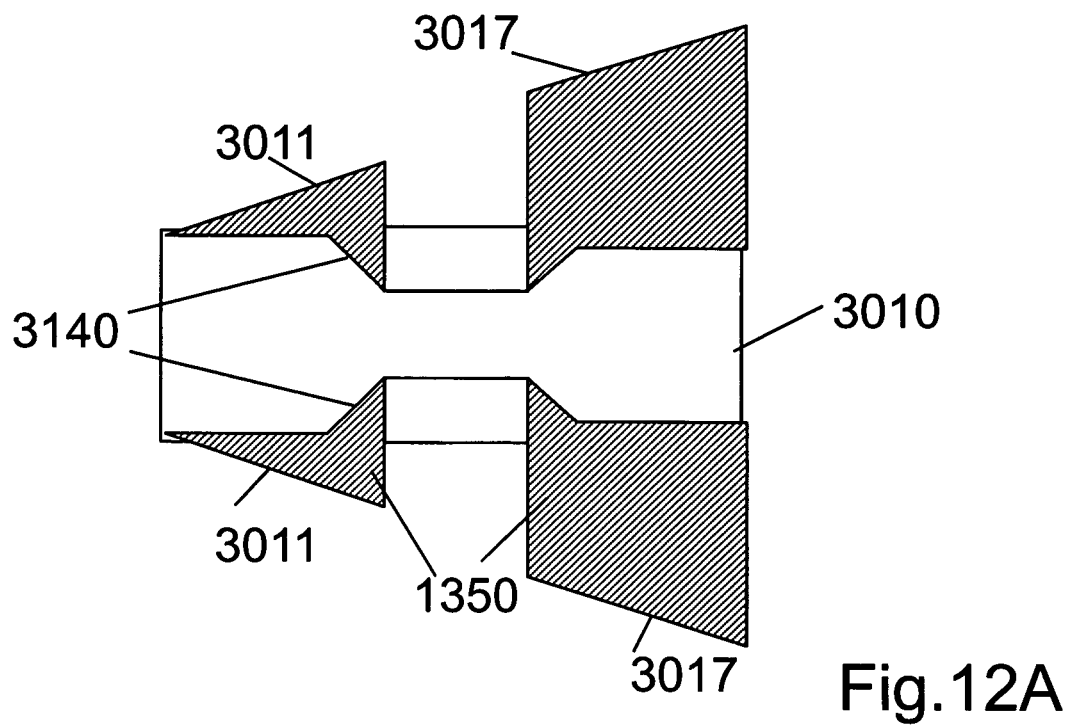
FIGS. 12 A & B show schematically a further embodiment of the present invention having an asymmetrical design.
Figure 12B:
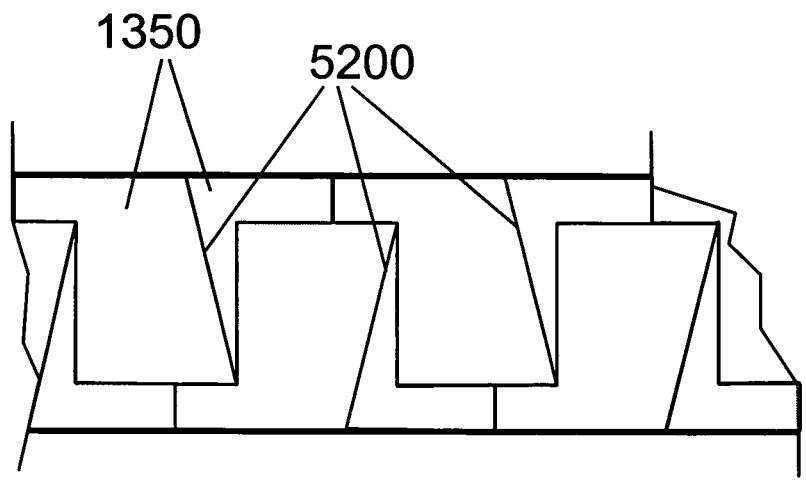

A skilled person will readily realize many variants and/or combinations, which may be designed by applying the principles of the present invention. As a further example, FIG. 12 A shows an article having tapered longitudinally extending side margins in the front and rear region (3011 and 3017 respectively), such that the laterally extending ears of the product have differing width in the front and back regions. Such a design may conveniently be made from a side panel web material 1350 as shown in FIG. 12 B with CD-cutlines 5200 being angled relative to the CD direction.

FIG. 13 exemplifies a design similar to the one as shown and explained in the context of FIG. 5, but with an added waist feature, here shown as a waist belt 5570. The material forming this belt may be added to the cut and separated side panel material 1350 in its MD direction (as indicated in FIGS. 13 A and B), thusly allowing easy processing, and it may be cut along cut lines 5560, as shown in FIG. 13 C. The material can be added and connected to the side panel material 1350 just prior to the connecting with the centre piece 3010 along a curved connecting line 1130, as depicted in FIG. 13 D. After the flipping (refer to FIG. 13 E showing the flipped sections hatched), the respective ends of the cut waist belt material 5570 may be connected along connecting lines or regions, here shown as connecting lines 5580. This connecting can be performed in a releasable manner, and this closure system would then be positioned in the front part of the article, which would be in contrast to most if not all conventional diaper designs, having a pair of closure elements laterally outwardly of the centre.

As yet a further example, FIG. 14 depicts an embodiment having only a single (here rear) integral leg hoop/side panel 1350. In analogy to the embodiment just described, the cut and separated side panel material 1350 is combined with the waist feature material 5570 oriented in its machine direction. FIG. 14 A shows still connected webs, whilst FIG. 14 B shows a pair of disconnected side panel material pieces with the waist feature material. The side panel material is then combined with the centre piece 3010, in FIG. 14 C shown with a curved connecting line 1130 in the crotch region 3015. After flipping, the article has only rear ears 1350 next to the rear region 3018 of the centre piece, which may during use be wrapped around the body and overlap with the front region of the centre piece 3012, optionally being connected thereto, such as by refastenable connecting means, and/or being held in place by the waist feature 5570. In order to complete the list of required operations, the various elements of centre piece, leg hoop, and side panel materials need to be connected, typically but not necessarily by a permanent bonding. This connecting may be by thermo-, pressure, or/ultrasonic bonding, or by the application of glue or adhesive, or by any other means as known to a skilled person. This connecting may be e.g. prepared by the application of adhesive on one or both elements, before these are combined.

The glue application may be such that one essentially continuous glue line 1241 is applied to the leg hoop piece (FIG. 2A), preferentially before this is cut. First (in the process flow direction), the adhesive is applied close to the longitudinal side margins in the front region in an essentially straight line. Further, the application nozzle is moved laterally inwardly and outwardly again, while the material is moving underneath, such that a curve-linear connecting line can be formed in the crotch region. In the rear region, the nozzle is held again stationary to create an essentially straight line along the longitudinal side margins in the rear region of the hoop material. Upon placement of the leg hoop piece onto the centre piece, the straight glue lines are positioned outwardly of the centre piece longitudinal side margin. After flipping the front and rear extensions of the hoop material, the straight glue lines are oriented essentially in cross direction 1020 of the product and facing the side panel cross directional cut line.

Optionally for certain embodiments of the side panel designs, glue may be applied to the front and rear extensions of the centre piece material and/or to the corresponding edge portions of the centre piece.

Optionally glue may be applied to corresponding connecting regions of said side panel material either as panels being pre-connected to or an integral part of said centre piece. In addition to these required process steps, a number of optional steps may be performed in order to arrive at a finished article, such as:

forming a pant like structure by forming a closed waist hoop;
applying closure and/or fastening features;
folding;
packing;
combing other web materials and/or web pieces and/or non web materials;
combining liquid handling and/or absorbing materials.

Working the details of any such additional features is fully within the routine of an ordinary person skilled in the art of producing pants or pant like structure, and are not considered limiting in any way for the present invention.

The invention claimed is:

1. A method for being carried out on a manufacturing equipment for the manufacture of an article for being worn on the lower torso of a wearer,
said article comprising
a centre piece comprising a front, centre and rear region corresponding to a front, crotch, and rear region during use,
thereby defining the length direction and orientation of the article and a width direction perpendicular thereto corresponding to the circumferential direction during use;
a first and a second leg hoop for encircling the legs of a wearer during use;
optionally side panels positioned in the lateral portions of the article and corresponding to the hip regions of the wearer during use;
optionally waist features for forming a waist hoop,
said equipment comprising
a closed loop operating means defining a machine direction (closed loop operating means-MD);
flipping equipment attached to said closed loop operating means or otherwise operatively associated to said closed loop operating means to allow an essentially zero differential speed movement relative to said closed loop operating means and comprising a support plate rotatably mounted around a rotating axis,
said rotating axis being co-planar with said closed loop operating means-MD and the width dimension of said article and at an angled orientation to said closed loop operating means-MD;
characterized in that said method comprises the steps of
(a) providing
(i) a centre piece web material for forming said centre piece of said article exhibiting a centre piece machine directionality essentially aligned with said length direction of said article;
(ii) one or more leg hoop material(s) for forming said first and second leg hoop of said article by providing
one or more separate leg hoop web material(s), essentially aligned with the MD direction of said centre piece web material,
or by forming leg hoop regions out of said centre piece web material preferably by an essentially longitudinally oriented separating line, preferably a cut line terminating in the crotch region of said centre piece web material,
(b) affixing extensions of said leg hoop material(s), but not a region between said extensions, to a support plate of said flipping equipment,
(c) rotating said support plate around said rotating axis, such that said extensions of said leg hoop material(s) are flipped over along a fold line which is angled by more than 0° but less than 90° relative to the overall orientation of the material, thusly being oriented at an essentially different angle to said closed loop operating means-MD.

2. A method according to claim 1, comprising one or more of the steps of:
introducing separate side panel material;
introducing waist web materials;
forming a pant like structure by forming a closed waist hoop;
applying closure and/or fastening features;
folding;
packing;
combing other web materials and/or web pieces and/or non web materials;
combining liquid handling and/or absorbing materials.

3. An article for being worn on the lower torso of a wearer obtainable by a method according to claim 1.

4. An article for being worn on the lower torso of a wearer obtainable by a method according to claim 2.

5. An article according to claim 3, as a body conforming pant, pant like article, absorbent article, a baby or adult incontinence diaper, a training pant, an adult incontinence article, or a feminine hygiene article.

6. An article according to claim 4, as a body conforming pant, pant like article, absorbent article, a baby or adult incontinence diaper, a training pant, an adult incontinence article, or a feminine hygiene article.

* * * * *